United States Patent [19]

Jacob et al.

[11] Patent Number: 4,734,094

[45] Date of Patent: Mar. 29, 1988

[54] CATHETER AND METHOD FOR CHOLANGIOGRAPHY

[76] Inventors: Erwin T. Jacob, Hanof str 19, Savyon, Israel; Burton Bronsther, 114 Cedar Ave., Hewlett Bay Park, N.Y. 11557

[21] Appl. No.: 871,819

[22] Filed: Jun. 9, 1986

[51] Int. Cl.⁴ .......................................... A61M 25/00
[52] U.S. Cl. .................................. 604/284; 604/101; 128/656
[58] Field of Search ............... 128/325, 344, 656, 658; 604/96, 101, 284

[56] References Cited

U.S. PATENT DOCUMENTS

| | | | |
|---|---|---|---|
| 2,819,718 | 1/1958 | Goldman | 604/96 |
| 3,392,722 | 7/1968 | Jorgensen | 604/284 X |
| 4,166,468 | 9/1979 | Haynie | 604/256 X |
| 4,230,119 | 10/1980 | Blum | 128/344 X |
| 4,263,917 | 4/1981 | Moss | 128/344 X |
| 4,547,187 | 10/1985 | Kelly | 604/284 X |

*Primary Examiner*—Dalton L. Truluck
*Attorney, Agent, or Firm*—Eliot S. Gerber

[57] ABSTRACT

A cholangiography catheter is used in the surgical removal of gall stones so that contrast liquid may be temporarily retained in the location of a patient's bile duct in order to take X-ray pictures of the bile duct. The catheter is a flexible and resilient "T"-shaped member having two air inflatable balloons, each connected in an arm of the catheter. The balloons may be independently inflated to close the drain lumen of the catheter and the bile duct.

5 Claims, 8 Drawing Figures

CATHETER AND METHOD FOR CHOLANGIOGRAPHY

BACKGROUND OF THE INVENTION

The present invention relates to medical devices and more particularly to a catheter used in the surgical removal of gall stones.

A relatively common, and troublesome, surgical procedure is the removal of "gall stones" caused by the concentration of bile.

Bile is a digestive juice secreted by the liver. The bile aids in the emulsification (dispersion), digestion and absorption of fat. The main constituents of the bile are bile salts (sodium glycocholate and sodium taurocholate), pigments (biliverdin and bilirubin) and cholesterol. Bile is stored, when not used, in the gall bladder, where it occasionally stagnates and forms concentrations of "stones" and is liable to infection.

The liver and gall bladder are connected to slender ducts (tubes) which are joined to the "bile duct" or the "common bile duct". The common bile duct is formed by the junction of the ducts leading from the liver and the gall bladder. The bile is delivered by the common bile duct (tube) to the first part of the small intestine (duodenum), which is the part at the outlet of the stomach.

The surgical removal of the gall stones is regarded as a relatively delicate and difficult surgical procedure. The surgeon should remove all the stones from the common bile duct. Yet the surgeon is unable to see into the common bile duct during the operation. If bile stones, or their particles, are not removed, they may form the nucleus of new stones which may require a later operation, months or years later. To avoid leaving any stones, or their particles, it is the accepted surgical practice to take a set of X-ray pictures after the surgeon has removed the stones. The X-ray pictures will show if any stones or stone particles remain, as well as their number and their location. If any stones or particles remain, the operation may continue and the patient may immediately be operated upon to remove them.

However, it is very difficult to obtain clear X-ray pictures (roentgenograph) of the common bile duct, i.e., called "cholangiography", even during an operation. To obtain worthwhile cholangiography pictures, a suitable X-ray sensitive liquid, called "contrast liquid" or "contrast", is introduced into the common bile duct and retained in the duct while the X-ray picture is taken. One method of temporarily retaining the contrast is to temporarily sew the duct shut to retain the contrast liquid in the duct while the X-ray pictures are taken. That method, however, is relatively slow and cumbersome and may, in some cases, injure the duct tissue.

OBJECTIVES AND FEATURES OF THE INVENTION

It is an objective of the present invention to replace the sewing of the bile duct to retain X-ray contrast liquid and to provide a specialized catheter for use in the common bile duct of a patient to temporarily retain the contrast liquid and improve the clarity of X-ray pictures of the common duct to aid in the complete surgical removal of gall stones and their particles.

It is a further objective of the present invention to provide such a common bile duct catheter that will permit the introduction, retention and release of an X-ray contrast liquid into the bile duct.

It is a further objective of the present invention to provide such a common bile duct catheter that will retain the contrast liquid without leakage and permit the contrast liquid to be removed after the X-ray pictures are taken.

It is a further objective of the present invention to provide such a common bile duct catheter that will not cause trauma to the common bile duct or surrounding tissue during the operation, thereby avoiding the trauma which may occur if the duct is temporarily closed using stitches or clamps.

It is a feature of the present invention to provide a cholangiography catheter adapted to be inserted in the common bile duct of a patient. After the catheter is in place, contrast liquid is flowed to the location of said bile duct and X-ray pictures are taken.

The catheter is a flexible and resilient tubular member of "T" shape, preferably formed of a silicone elastomer material. It has a perpendicular branch and first and second opposite side branches forming drain lumens, the three branches meeting at a common point. Each side branch has a balloon (first and second balloons) comprising a section of the branch wall. Each balloon consists of an inner flexible wall and an outer flexible wall forming between them an interior space. The balloons are individually expanded by the introduction of air and collapsed by the withdrawal of the air.

A first air channel in the perpendicular branch and the first branch leads to the interior space of the first balloon. A second air channel in the perpendicular branch and the second branch leads to the interior space of the second balloon. The air channels each lead from the perpendicular branch to an outside controlled source of air.

To take an X-ray picture, the second balloon is expanded to close the bile duct and the catheter drain lumen; the first balloon is partially expanded; the contrast liquid is introduced between the balloons; and the second balloon is expanded to close the bile duct and the second drain lumen to retain the contrast liquid between the balloons.

BRIEF DESCRIPTION OF THE DRAWINGS

Other objectives and features of the present invention will be apparent from the following detailed description of the invention, taken in conjunction with the accompanying drawings, in which.

DETAILED DESCRIPTION OF THE INVENTION

As shown in FIGS. 1-8, the catheter of the present invention is used for the localized control of X-ray contrast liquid, i.e., "contrast". The catheter is formed of a flexible and resilient material, preferably medical grade silicone elastomer, a rubber-like artificial plastic resin which is approved by use in patients.

The size of the tubing may vary, depending on the patient, but preferably is No. 14 French tubing or No. 16 French tubing or No. 18 French tubing. The preferred size of the two balloons, the recommended air volume to fully expand the balloons and the recommended air volume for partial collapse of the balloons are set forth in the chart below.

Figure 1:
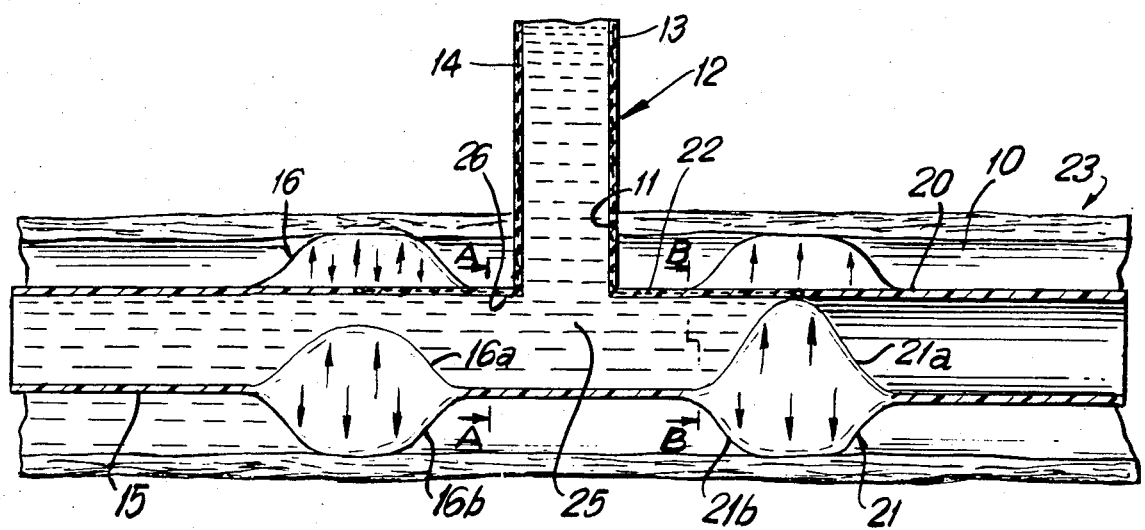
FIGS. 1 and 6 are enlarged side cross-sectional views of the catheter of the present invention.

As shown in FIG. 1, the common bile duct 10, shown as a tubular tissue member, has a hole 11 opened by the surgeon. The T-tube catheter 12 is of the general shape of a "T" and comprises, in general, three tubular branches. The perpendicular branch 13 of catheter 12 is a tubular member, shown cross-section in FIG. 1, in which two small air channels 14 and 21 lead, outside of the patient, to two carefully controlled sources of air 30,31 (shown in FIG. 7).

Figure 2:
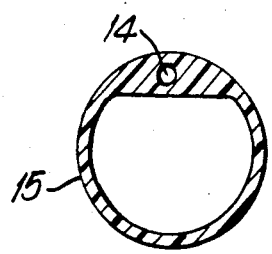
FIGS. 2 and 3 are cross-sectional views taken along lines A—A and B—B of FIG. 1.
Figure 3:
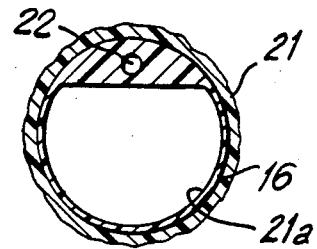

The first side branch 15, the left branch as seen in FIG. 1, is also a tubular member which lies within the bile duct 10. The air channel 14 continues in the branch 15 until it reaches the first (proximal) balloon 16. As shown in FIG. 2, the cross-section of the branch 15, the top portion of the tube is thickened in order to hold the air channel 14. As shown in FIG. 3, at the balloon 16 the side wall of branch 15 is thin, compared to the side wall of FIG. 2.

Each of the two balloons is formed of two thin flexible walls, preferably of 0.015-0.025 mm thickness, so that both walls together have a thickness of 0.3-0.5 mm. An air channel opens to the interior space of each balloon, i.e., between its walls, and the balloon walls are sealed air-tight to the branch. Balloon 16 comprises inner wall 16a and outer wall 16b; and balloon 21 comprises inner wall 21 and an outer wall 21b, see FIG. 1.

Figure 6:
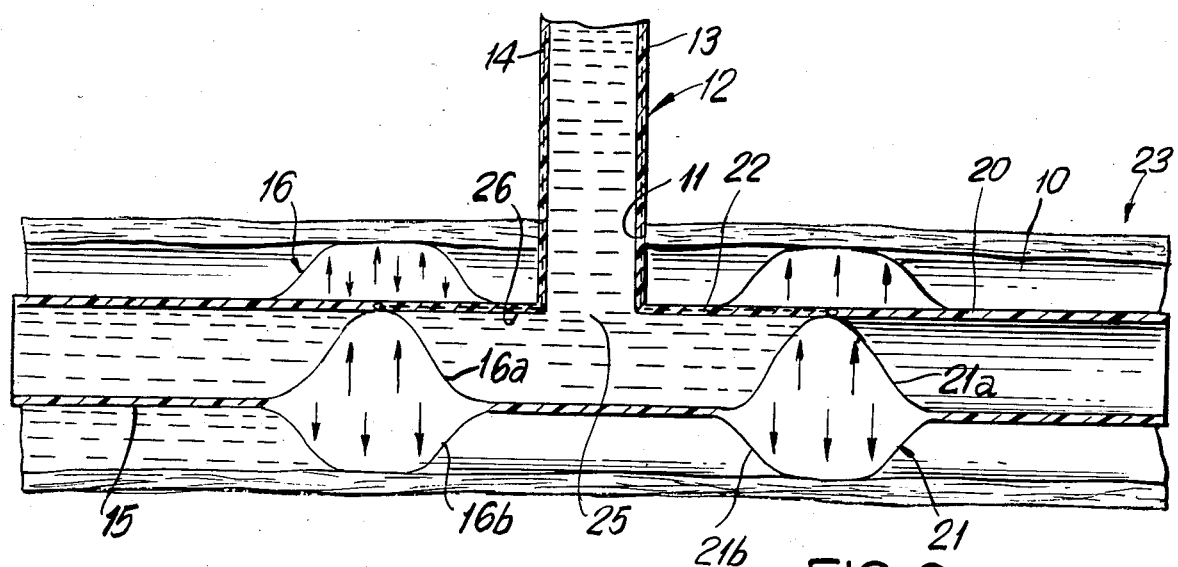
Figure 7:
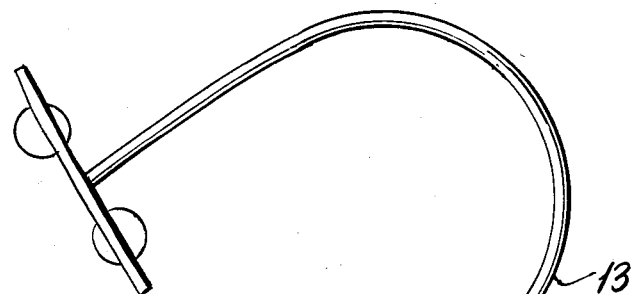
FIG. 7 is a top plan view of the catheter of the present invention.
Figure 8:
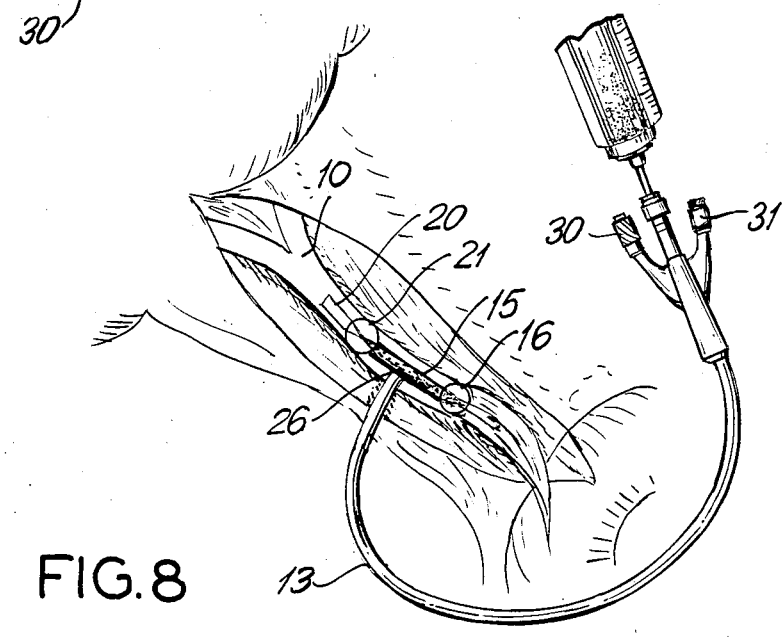
FIG. 8 is a perspective view, similar to the view of FIG. 6, showing the contrast liquid in the common bile duct.

The balloon 16 expands when filled with air. In FIG. 1 the balloon 16 is partially expanded so that it fills the space between the branch 15 and the duct 10, but does not close off the interior "drain lumen" of branch 15. This is Duct Occlusion Pressure (DOP). In FIG. 6 the balloon 16 is fully expanded so that it closes the drain lumen and the duct 10 of the catheter and the duct 10, i.e., this is Tube Occlusion Pressure (TOP).

The second branch 20 is of the same construction as the first branch 15 and aligned along a common imaginary central axis. The branch 20 includes a second (distal) balloon 21 which is connected to the air channel 21 which runs in the branch 20 and also in the branch 13.

Figure 4:
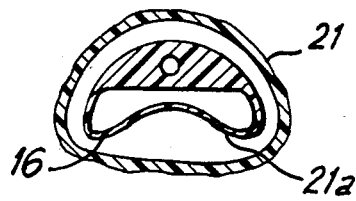
FIGS. 4 and 5 are cross-sectional views, similar to FIG. 3, but with the balloon in two stages of its collapse.
Figure 5:
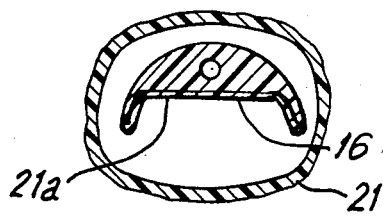

As shown in FIG. 4, the balloons 16 and 21 may be partially inflated, or, as shown in FIG. 5, may be fully deflated. The inflation of the balloons 16 and 21 is controlled by the amount of air which is pumped into the balloons from the exterior sources of air 30 and 31.

In a surgical procedure, when it is desired to obtain an X-ray of the common bile duct (cholangiography), the first and second branches 15 and 20 of the T-tube catheter 12 are placed by the surgeon in the common bile duct 10 through the opening 11. The air pressures mentioned in this example will be in connection with a catheter of 14 French tubing size, although, as shown by the chart below, the preferred air pressures will vary with the size of the tubing. The balloon 21 is inflated with about 2 ml. of air. This completely inflates the balloon 21, as shown in FIG. 1, so that it occludes (closes) the distal end 23 of the common bile duct 10. In addition, the balloon occludes the drain lumen of the catheter, so that contrast liquid may not flow past the balloon 21 within the catheter. The proximal balloon 16 is then partially inflated, with 1.0-1.5 ml. of air pressure, as shown in FIG. 1. The contrast liquid 25 is then injected through the internal drain lumen 26 of the catheter. The contrast liquid 25 does not flow past the balloon 21. When the space in the catheter between the balloons 16 and 21 is filled with contrast liquid 25, the ballon 16 is further inflated, with 0.5-1 ml. of additional air, to fully inflate the proximal balloon 16. When fully inflated, the proximal balloon 16 completely occludes the bile duct 10 and the drain lumen of catheter and retains the contrast liquid between the two balloons 16 and 21.

At this time, with the contrast liquid 25 contained between the two balloons 16 and 21, a series of X-ray pictures are taken. The contrast liquid will act, in the X-ray pictures, to highlight any gall stones or stone particles which may be lodged in the bile duct.

After the X-ray pictures are taken, the proximal balloon 16 is partially collapsed, as shown in FIG. 4, and the contrast liquid is drained from within the catheter. The two balloons 16 and 21 are then fully collapsed and the catheter withdrawn from the bile duct and from the patient.

The balloons 16 and 21, when fully inflated, prevent the contrast liquid from flowing (i) from between the outer wall of the catheter and the bile duct, and (ii) from within the drain lumen of the catheter.

The preferred balloon capacities of each of the two balloons and the air volume recommended for their partial expansion and complete expansion depends upon the tube size of the catheter. The chart below provides the recommended capacities and air volumes:

| Size of Tube Fr. | Balloon Capacity ml | Air volume to fully expand balloon and occuld drain lumen and bile duct (TOP) ml | Air volume to partially expand balloon and occuld bile duct (DOP) ml |
| --- | --- | --- | --- |
| 14 Fr. | 2 | 2 | 1-1.5 |
| 16 Fr. | 3 | 3 | 2-2.5 |
| 18 Fr. | 4 | 4 | 3-3.5 |

It is preferred that the perpendicular branch have some frictional engagement so that it remains in position. For this purpose it may be covered with an elastometer web or a sleeve of elastomeric material, such as rubber, having greater frictional engagement than silicone.

It will be understood that the examples of air volume, in the chart above, are only typical examples. The actual air volumes used will primarily depend upon the size of the common bile duct being operated upon.

In the example set forth above, the proximal balloon is fully expanded (TOP) and the distal balloon is partially inflated (DOP) to obtain a selective distal cholangiogram. Alternatively, and not shown, the proximal balloon is partially expanded (DOP) and the distal balloon is fully expanded (TOP) to obtain a selective intrahepatic radiological delineation. In both cases the technique is used post-operatively or to obtain better X-ray imaging of the proximal or distal common bile duct, interoperatively.

In addition, inflation of both balloons leaves a "bile free" zone which can be used to dry out a leak arising from choledocotomy.

What is claimed is:

1. A cholangiography catheter adapted to be inserted in the common bile duct of a patient in order to introduce and retain contrast liquid in the location of said bile duct in order to take X-ray pictures of the bile duct;

the catheter being a flexible and resilient tubular member of "T" shape and having a perpendicular branch and first and second opposite branches forming drain lumens, the three branches joining at a common point;

said catheter having means for closing both said bile duct and said drain lumens comprising a first balloon connected in said first branch and a second balloon connected in said second branch, each balloon comprising a section of the branch wall and consisting of an inner flexible wall and an outer flexible wall forming between them an interior space, said balloons being individually expanded by the introduction therein of air and collapsed by the withdrawal therefrom of said air;

a first air channel in said perpendicular branch and said first branch leading to the interior space of said first balloon, a second air channel in said perpendicular branch and said second branch leading to the interior space of said second balloon;

the said air channels each leading from the perpendicular branch to separate outside controlled sources of air;

wherein, to take an X-ray picture, the second balloon is expanded so said outer wall completely closes the bile duct and said inner wall completely closes said first drain lumen and the firt balloon is partially expanded, the contrast liquid is introduced between the balloons and the first balloon is then expanded so said outer wall completely closes the bile duct and said inner wall completely closes said second drain lumen and thereby temporarily retain the contrast liquid in the bile duct and drain lumen.

2. A cathether as in claim 1 wherein said catheter is of silicon elastomer material.

3. A catheter as in claim 1 wherein said perpendicular branch is at least partially covered by a material having greater friction than the material of the other branches.

4. A catheter as in claim 1 wherein said perpendicular branch is at least partially covered with rubber.

5. An improved method of X-ray picture cholangiography including the steps of:

surgically incising the common bile duct of a patient;

inserting a hollow catheter balloon means into said incised bile duct;

the catheter being a flexible and resilient tubular member of "T" shape and having a perpendicular branch and first and second opposite branches forming drain lumens, the three branches joining at a common point;

inflating said balloon means;

injecting a radiopaque contrast agent into said bile duct through said perpendicular branch;

subjecting said injected bile duct to roentgenography whereby any stones therein can be detected;

deflating said catheter balloon means and removing any such stones as may be detected;

repeating said steps of inserting, inflating, injecting, subjecting and deflating until said bile duct is free from stones; and removing said cahteter from said bile duct and the patient after all of the stones have been removed;

the improvement comprising:

before taking the first X-ray picture, inflating a second balloon to completely close the bile duct and first drain lumen and partially inflating a first balloon;

introducing the contrast agent between the balloons and then completely inflating the first balloon to close the bile duct and second drain lumen and thereby temporarily retain the contrast liquid in the bile duct and drain lumen;

the balloon means comprising a first balloon connected in said first branch and a second balloon connected in said second branch, each balloon comprising a section of the branch wall and consisting of an inner flexible wall adapted to close the bile duct and an outer flexible wall adapted to completely close the drain lumen forming between them an interior space, said balloons being individually expanded by the introduction therein of air and collapsed by the withdrawal therefrom of said air;

the inflation of the first and second balloons being by the introduction of pressurized air into said balloons from respective separate outside controlled sources of air which are connected to separate first and second air channels;

the first air channel being in said perpendicular branch and said first branch and leading to the interior space of said first balloon and the second air channel being in said perpendicular branch and said second branch and leading to the interior space of said second balloon.

* * * * *